United States Patent
Fleche et al.

[11] Patent Number: 5,817,780
[45] Date of Patent: Oct. 6, 1998

[54] PROCESS FOR THE ALKALINE OXIDATIVE DEGRADATION OF REDUCING SUGARS

[75] Inventors: Guy Fleche, Hazebrouck; Pierrick Duflot, Lacouture, both of France

[73] Assignee: Roquette Freres, France

[21] Appl. No.: 875,353

[22] PCT Filed: Dec. 5, 1995

[86] PCT No.: PCT/FR95/01598

§ 371 Date: Oct. 20, 1997

§ 102(e) Date: Oct. 20, 1997

[87] PCT Pub. No.: WO97/20860

PCT Pub. Date: Jun. 12, 1997

[51] Int. Cl.⁶ .............................. C07H 1/00; C07H 3/00; C07H 7/027
[52] U.S. Cl. .................. 536/18.6; 536/18.5; 536/124
[58] Field of Search ................... 536/18.5, 18.6, 536/124

[56] References Cited

U.S. PATENT DOCUMENTS 2,587,906  3/1952  Schmidt .
4,125,559  11/1978  Scholz et al. .

FOREIGN PATENT DOCUMENTS 0232202    1/1987   European Pat. Off. .
0 232 202  8/1987   European Pat. Off. .
2 722 200  1/1996   France .
2722200    12/1996  France .
60925-3    7/1970   Luxembourg .
2 075 502  11/1981  United Kingdom .
WO 93/19030 9/1993  WIPO .

OTHER PUBLICATIONS

Z. Wirtschaftsgruppe Zuckerindustrie, Tech. T1, 1935, 85 pp. 546–552.
Bull. Soc. Chim. Fr., (1959) 1353–1362 by Dubourg and Naffa.
Starch / stärke 43 No. 5, pp. 194–198; 1991.
Carbohydrate Research, 214 (1991) pp. 71–85.
Carbohydrate Research, 203 (1990) pp. 287–289.
Carbohydrate Research, 116 (1983) pp. 61–69.
Vudrinen, T. Carbo. Res. 116: 61–69, 1983.
Hendriks et al. Carbo Res. 214: 71–85, 1991.

*Primary Examiner*—Gary L. Kunz
*Attorney, Agent, or Firm*—Henderson & Sturm

[57] ABSTRACT

A process for the alkaline oxidative degradation of an ose, a ulose, their polymers or their mixtures, in aqueous solution in the presence of a redox pair consisting essentially of a mixture of 2-anthraquinone monosulfonic acid and hydrogen peroxide, wherein oxidizing gas is air and said air is stir-beaten and introduced into the reaction medium under stirring conditions and at a flow rate such that the oxygen-saturation of the reaction medium leads to the production of a pink color in this reaction medium.

12 Claims, 1 Drawing Sheet

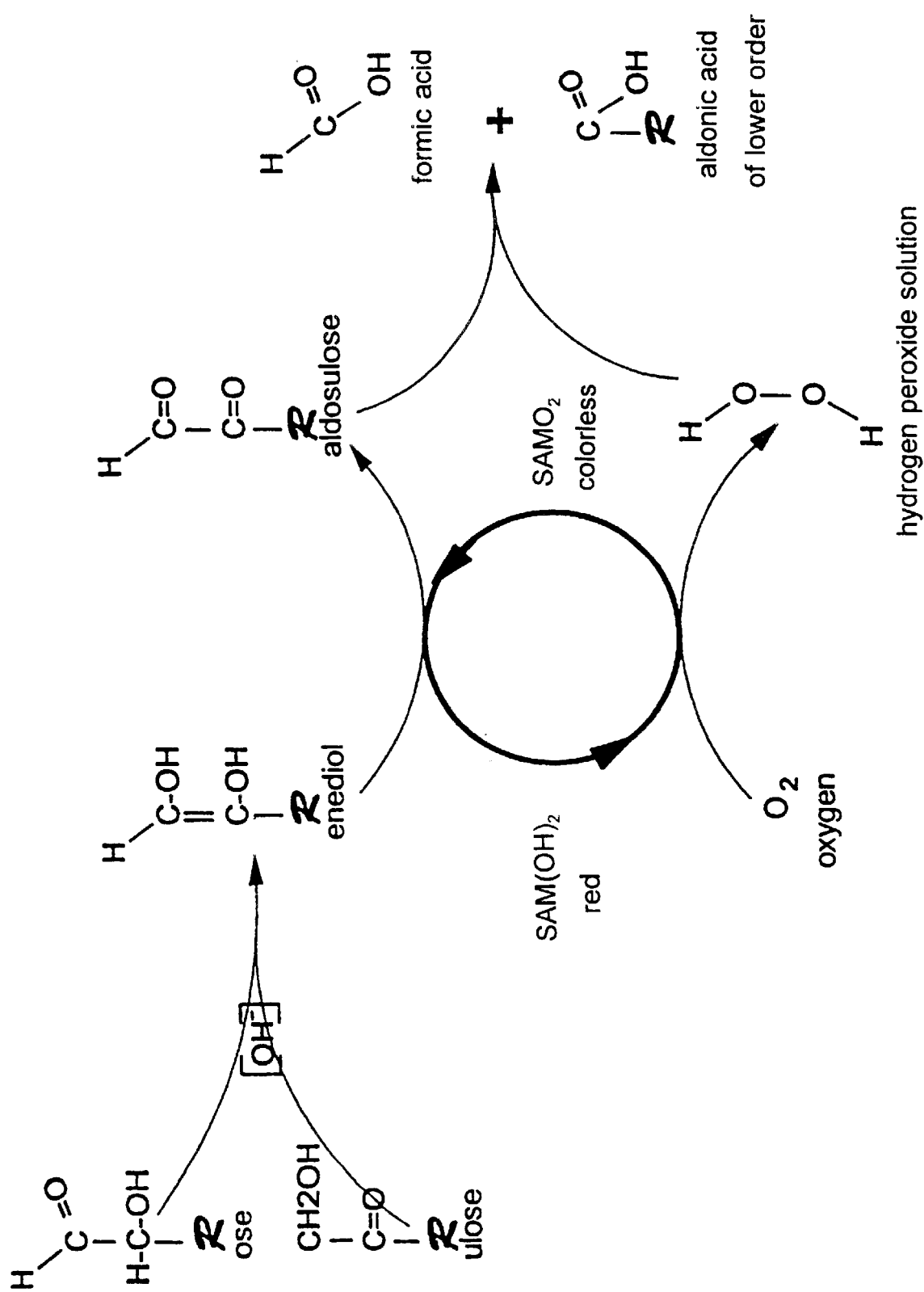

PROCESS FOR THE ALKALINE OXIDATIVE DEGRADATION OF REDUCING SUGARS

"This application is a 371 of PCT/FR95/01598 filed Dec. 5, 1995."

The present invention relates to an improved process for the alkaline oxidative degradation of oses or uloses and their polymers.

The expression oses, uloses and their polymers is understood to refer to any reducing sugar or carbohydrate of he polyhydroxyaldehyde or polyhydroxyketone type (or any compound derived therefrom, such as ketoaldonic acids, uronic acids, acetyl, amino, alkyl, carboxymethyl, etc. derivatives) or polymers or polysaccharides which are capable of liberating these same compounds by hydrolysis.

As novel industrial products, the invention also relates to dextrins or hydrolysates of native or modified starch which have been thus degraded, as well as the products obtained by alkaline oxidative degradation of polysaccharide or polyholoside hydrolysates such as hydrolysates of cellulose, of dextrans, of arabans, of xylans, of arabinoxylans, of fructans or of inulin or hydrolysates of heteropolyholosides such as gums, hemicelluloses, mucilages or pectins, or alternatively synthetic polymers obtained by polymerization of various monomeric oses in the presence of acid and at high temperature, such as polydextrose, which is a highly branched glucose polymer.

One advantage of oxidatively degrading oses, and especially their polymers, in a kaline medium lies in the production of hydroxylated molecules which become carriers of carboxyl groups. It is known that such molecules show advantageous sequestering properties.

These sequestering properties may be exploited in the field of cements, mortars and concretes in which glucose syrups oxidized by bleach have already been proposed as setting retardants, for example in British patent application GB 2,075,502.

They may also be exploited in the field of detergency, in which glucose syrups, this time oxidized with a gas containing oxygen in the presence of a catalyst based on a noble metal, have been proposed for cleaning glass or metal articles, or as additives for detergents, as is dealt with, for example, in European patent application EP 232,202.

The alkaline oxidation processes described in these two patent applications have in common the fact that they use weakly alkaline media with a pH of between 7.5 and 11, and that oxidation of the reducing functions is carried out with virtually no loss of carbon and thus without degradation, that is to say that under the conditions described, the oxidation of the reducing function of an ose essentially gives the aldonic acid of the same order, which thus has the same number of carbon atoms. The oxidized glucose syrups thus obtained are therefore composed essentially of gluconate originating from the oxidation of glucose, of maltobionate originating from the oxidation of maltose, and, more generally, of dextrin-gluconates originating from the oxidation of polysaccharides with a higher degree of polymerization.

However, neither of these two processes allows the total conversion of the reducing functions into carboxylic acid functions, and the products thus obtained always have a non-negligible residual reducing power. In the case of oxidation with bleach, even overoxidation phenomena occur, leading to the creation of reductive ketone functions from the secondary alcohol groups of the oses. In the case of oxidation with oxygen, catalysed by a noble metal, these overoxidation phenomena are not observed, but, although this oxidation reaction takes place at a relatively low pH, the appearance of ketone functions cannot be avoided, these functions forming by alkaline isomerization of the hemiacetal functions and not being oxidizable by the process used.

Thus, in the case of a 33 DE glucose syrup oxidized with bleach according to patent application GB 2,075,502, it can hardly be envisaged to go down to residual reducing sugar levels, expressed as glucose and measured by the Bertrand method, of less than 4.5%, and in the case of European patent application EP 232,202, this content can hardly be lowered to values below 1.7%.

Although the products obtained by these processes show excellent complexing properties, they are relatively incompatible with washing formulations of high pH since the powders thus formulated turn yellow over time by alkaline degradation of these residual reducing sugars.

In addition, the presence of chlorides provided by the bleach, and the cost of the catalysts based on noble metals are not features which stand out in favor of the use of these oxidized glucose syrups in cements, concretes and mortars.

The reason for this is that chlorides corrode metal armatures and the extremely low cost of hydraulic compositions does not allow them to be supplemented with expensive products.

British patent application GB 2,075,502 also describes a process of degradation, in an alkaline medium which this time is not oxidative, of glucose polymers, which also leads to the formation of acids by degradation of the reducing ends of the monomers and polymers of which the glucose syrups are composed. In contrast with the previous processes, this degradation of the reducing functions is carried out with a loss of carbon, that is to say that under the conditions described in Examples 4 and 5 of that patent application, the reducing oses are essentially converted into carboxylic acids of lower orders, containing 1, 2, 3, 4 or 5 carbon atoms less than the ose from which they are derived.

The degraded glucose syrups thus obtained are thus formate, acetate, lactate, saccharinate or arabinonate compounds, but glycolate, dihydroxybutyrate, metasaccharinate, isosaccharinate and deoxypentonate are also found therein in large amounts, the species being formed at the expense of the glucose degraded. Dextrin-saccharinates or dextrin-aldonates are also found therein, including a small amount of dextrin-arabinonates which are formed at the expense of the glucose polymers.

The degraded glucose syrups obtained in this way still contain at least 5% residual reducing sugars. They are moreover highly colored, which immediately excludes them from the field of detergency.

However, although they are produced relatively economically, and although it may thus be envisaged to use them as setting retardants in hydraulic compositions, they do not give reproducible results since slight variations in the pH or in the degradation temperature lead to considerable variations in their composition, as regards both the acids formed and the length of the residual polysaccharide chains which, as is pointed out in this patent application, may readily be hydrolyzed, even in slightly alkaline medium and at low temperature.

This process, which is difficult to reproduce from one manufacturing batch to another, therefore does not make it possible to obtain products of repeatable performance, although this is highly desirable in an application such as setting retardants for cements, mortars and concretes, in which too fast a setting during transportation or too slow a setting during uncasing may hare extremely damaging consequences.

Another advantage of oxidatively degrading ose polymers, and especially their monomers, in alkaline medium lies in the most exclusive possible Production of aldonic acids containing only one carbon less than the ose from s which they are derived.

Such processes have been known for a very long time and have been applied to the alkaline oxidative degradation, using oxygen, of monoses or of mono-uloses, or even of certain reducing disaccharides such as lactose, maltose and palatinose.

However, in contrast with the processes detailed above, which use only weakly alkaline reaction media with a pH of not more than 11.0, these other processes use very strongly alkaline reaction media with a pH which is at least greater than 12.0 and which are thus capable of degrading the carbon skeleton of the polymers, but which make it possible to remove virtually all of the reducing sugars by lowering their content to residual values which are generally less than 0.%. Indeed, they are effective on the ketone functions.

However, to the Applicant's knowledge, these processes have only been used on monomeric or dimeric reducing oses and are based on the process developed by Nef and perfected by Spengler and Pfannenstiel (Z. Wirtschaftsgruppe Zuckerindustrie, Tech. Tl, 1935, 85, 546–552). By using oxygen gas to improve upon the Nef process which used air, the above authors managed to oxidatively degrade glucose, fructose, mannose and arabinose in strongly alkaline medium, in molar yields close to 75%, essentially into arabinonic acid for the first three sugars and into erythronic acid for the pentose.

This type of alkaline oxidative degradation process results mainly, on the one hand, in the degradation cf the sugar into aldonic acid comprising one carbon atom less than the starting reducing sugar and, on the other hand, into formic acid. Their main interest lies in the production of this aldonic acid of lower order.

They effectively make it possible to gain access to 5 shorter molecules which may serve as a basis for many chemical syntheses. Thus, the oxidation of L-sorbose according to these processes makes it possible to obtain L-xylonic acid, hydrogenation of the lactone of which gives xylitol. 10 These molar yields of 75% arabinonic acid are achieved with glucose in aqueous medium and at atmospheric pressure on condition that finely divided oxygen is employed and using at least 3 mol of hydroxyl anion $OH^-$ per mole of glucose used.

Under the same conditions of high alkalinity and of oxidation with pure oxygen at atmospheric pressure, Schmidt has described, in U.S. Pat. No. 2,587,906, the production of molar yields of 65% crystalline potassium arabinonate from invert sucrose. In the presence of certain promoters which may act as a redox pair, and in particular methylene blue, it was possible to raise this yield to 82%. However, this yield fell to 77.7% when the oxidation was carried out with air instead of oxygen.

This type of alkaline oxidative degradation, which is effective both on hemiacetal functions and on ketone functions, also entails the formation of by-products such as, in particular, carbonic acid, oxalic acid, glyceric acid, glycolic acid, lactic acid, erythronic acid and, of course, fornic acid, which are obtained in a molar yield of about 25% from glucose when the alkalinity conditions are such that they allow a 75% yield of arabinonate. Formic acid is always produced in yields close to 100% of the stoichiometry.

An excellent study of the Spengler-Pfannenstiel process will be found in the publication by Dubourg and Naffa (Bell. Soc. Chim. Fr., (1959) 1353–1362) who report the alkaline oxidative degradation, in the presence of oxygen gas, arabinose, glucose, galactose and maltose. These authors had also noted that the presence of methanol or of redox promoters such as hydroquinone or resorcinol in the reaction medium favored the oxidation of glucose into arabinonic acid by increasing slightly both the rate of oxidation and the yield of the reaction.

They also showed that the use of amounts less than 3 mol of hydroxvl anions $OH^-$ per mole of reducing sugar used was reflected in a dramatic lowering in the yield of aldonate of lower order. For example, in the absence of promoter and even when the oxidation is carried out using pure oxygen, the use of 2 mol of potassium per mole of glucose allows the production of only 58% arabinonate.

The U.S. Pat. No. 4,125,559 by Scholz and Gotsmann recommends working under oxygen pressures ranging up to 40 bar and claims to obtain arabinonate yields of up to 98%.

In the example provided in that patent, the sodium hydroxide/glucose molar ratio is 3.5 and the oxygen pressure is 21.5 bar.

Vuorinen, Hyppanen and Sjostrom (Starke, 43 No. 5, p. 25 194–198; 1991) managed to oxidize glucose into arabinonate in a yield of 78%, using only 2.17 mol of sodium hydroxide per mole of glucose in water and under an oxygen pressure of 26 bar (2.6 megapascals). This yield could be raised to 86% in the presence ot a redox promoter: SAM (sodium salt of 2-anthraquinone monosulfonic acid) in an alkali/sugar molar ratio of only 2.33, but in the presence of 0.96 kg of methanol per kg of water in the final reaction medium, and at a more reasonable oxygen pressure which was, however, 6 bar (0.6 megapascals). According to these authors, the explanation of this good yield is that in methanolic medium the mass transfers are faster and the oxygen is more soluble, which allows a higher selectivity and a higher yield for the alkaline oxidative degradation reaction.

It will also be noted that the presence of methanol in the reaction medium makes it possible to crystallize the potassium arabinonate as it forms and thus to shift the direction of the reaction favorably.

Vuorinen again, in patent application PCT 93/19030, Example 7, demonstrates that it is possible to oxidize sorbose into xylonic acid in a molar yield of 69% by using only 2.06 mol of alkali per mole of sugar, but on condition that the process is carried out under an oxygen pressure of 10 bar and in the presence of about 100 g of methanol per 200 g of water.

Hendricks, Kuster and Marin (Carb. res, 214 (1991) 71–85) have shown that the selectivity and rate of oxidative degradation of glucose, galactose and lactose could individually be increased by the use, in the reaction medium, of a redox pair consisting of the sodium salt of 2-anthraquinone monosulfonic acid (SAM) and aqueous hydrogen peroxide solution, on condition that oxygen is used at a pressure of 1 bar (0.1 megapascal) in order for the reaction medium to be saturated (the SAM should remain in its colorless oxidized form whereas its reduced form is dark red). These authors also use very alkaline media, containing three moles of hydroxyl anions $OH^-$ per mole of reducing sugar used.

By means of this process, the yields of arabinonate reach 95 to 98% of the theoretical yield starting with glucose. They are lower when a diholoside is used, since they achieve only 90 to 95% of galactopyranosyl 1-3arabinonate from lactose. The authors explain this lowering of selectivity by alkaline hydrolysis of the beta 1 →4 oside bond of this disaccharide, brought about by the high pH at which the reaction takes place (13.8 to 14.5). However, they conclude therefrom that their process may be applied generally to carbohydrates.

Whether they are considered together or separately, measures consisting in:
  using pure oxygen
  working under pressure
  using excesses of alkalis
  using solvents had the incontestable results of contributing towards the increase in the selectivity and yield of the processes for the alkaline oxidative degradation of monomeric or dimeric oses and uloses.

The use of promoters has made it possible to further improve this performance.

However, at the current time, there is still no process which makes it possible to oxidize a reducing ose, ulose or diholoside in such a specific and complete manner that it gives virtually only the corresponding aldonic acid of immediately lower order (thus containing only one carbon atom less) and, of course, formic acid in equimolar amounts, and which does not make use of these expensive, or even dangerous, means, namely the use of pure oxygen, high pressures, excess alkalis, and organic solvents.

Similarly, at the present time, there is still no process which makes it possible to oxidize virtually exclusively into polyholoside-aldonate, and more precisely into dextrin-aldonate, an ose or ulose polymer, and more preferably a hydrolysate of native or modified starch, to the point at which almost all of the reducing sugars are removed and without shortening of the carbon skeleton of the polymer as a result of hydrolysis of some of its oside linkages.

By limiting the oxygen-saturation of the reaction medium and by going against the teachings of the prior art, by foregoing all the measures mentioned above whose usefulness now no longer appeared to be in any doubt, the Applicant Company, which has become aware of these problems and the need to provide a solution thereto, has succeeded in developing a process for the alkaline oxidative degradation of oses or ulose and even of their polymers, which is finally free of the drawbacks already mentioned.

BRIEF DESCRIPTION OF FIGURE

The FIGURE is a schematic of the instant applicant's alkaline oxidative degradation of reducing sugars.

According to the invention, this process of alkaline oxidative degradation, which consists in oxidizing an ose, a ulose, their polymers or their mixtures, in aqueous solution in the presence of a redox pair consisting of a mixture of SAM and hydrogen peroxide, is characterized in that the oxidizing gas is air and in that this air is stir-beaten and introduced into the reaction medium under stirring condition and at a flow rate such that the oxygen-saturation of the reaction medium leads to the production of a pink color in this reaction medium.

Indeed, it is known that the reduced hydroquinone anion SAM(OH) develops an intense brown-red color whereas the oxidized quinone molecule $SAMO_2$ is entirely colorless. The pair consisting of SAM quinone and its hydroquinone thus also behaves as a colored redox indicator which allows the level of saturation with oxygen dissolved in the reaction medium to be estimated visually.

Under these reduced but, however, surprisingly sufficient oxygenation conditions, indicated by a pink color of the SAM, the Applicant Company has noted that the reducing sugars were oxidized almost entirely selectively and completely into aldonic acid of immediately lower order and into formic oid without any appreciable formation of other acids originating from the non-oxidative alkaline degradation of these reducing sugars (lactic, metasaccharinic, dihydroxy-butyric acid, etc.).

These reduced oxygenation conditions may readily be obtained, and this constitutes an enormous financial advantage, without pure oxygen or without oxygen-enriched air and without the use of high pressures or of alcohol for promoting the mass transfers or increasing the solubility of oxygen in the reaction medium.

In general, in the context of the process which is the subject of the invention, it suffices that the air pressure be sufficient to overcome the hydrostatic pressure created by the liquid column present in the reactor. Care will also be taken to ensure that the venting of the gases from the reactor takes place without any constraint and at atmospheric pressure.

The Applicant Company believes that, under the conditions described for the process of the invention, oxygen is not present in sufficient quantities to oxidize directly the reducing sugars, or rather the enols which form under alkaline conditions. The reason for this is that it is known that this direct action of oxygen is not entirely selective and that it results in, besides the aldonic acids of immediately lower order, the production of acids derived from overoxidation of these reducing sugars into short-chain hydroxy-carboxylic acids (oxalic acid, glycolic acid, glyceric acid, tartronic acid, etc.), or even carbonic acid.

The Applicant Company also believes that in the process in accordance with the invention, the amount of oxygen present in the reaction medium is, in fact, just sufficient to regenerate, with concomitant synthesis of hydrogen peroxide, the quinone form of the anthraquinone ($SAMO_2$), which selectively oxidized the reducing sugar or more exactly its enediol into aldosulose, by becoming converted into the hydroquinone form ($SAM(OH)_2$). The hydrogen peroxide thus formed is immediately used to oxidize specifically, and virtually without formation of by-products, the aldosulose into aldonic acid containing one carbon atom less, on the one hand, and into formic acid, on the other hand.

For greater ease of understanding of these chemical reactions, reference may be made to the single FIGURE of the present text.

There is thus also in the process of the invention no excess of hydrogen peroxide in an amount such that it is capable of oxidizing in a directly detectable manner the reducing sugar to the state of formic acid and water by homolytic cleavage of its carbon chain. The reason for this is that this process would gradually lead to the complete degradation of an aldose by successive and rapid shortening of its carbon chain, the starting aldose itself being converted into another aldose of immediately lower order, on the one hand, and into formic acid, on the other hand. (H. S. ISBELL et al. Carbohydrate Research, 203 (1990) 287–289).

This extreme selectivity of the alkaline oxidative degradation of oses or uloses and of their polymers, obtained by the specific oxygen-saturation conditions of the process according to the invention, makes it possible to reduce to virtually the stoichiometric amount, which is slightly above 2 mol, the alkali to be used per mole of reducing sugar to be oxidized. Even under these conditions, the selectivities and yields obtained remain excellent.

This is made possible only by the virtual absence of interfering reactions, reflected by the appearance of short-chain acids, and only one mole of formic acid and one mole of aldonic acid are to be neutralized per mole of reducing sugar used.

Only a slight reserve of alkalinity is necessary to give the reaction medium, until the end of the reaction, a pH which is sufficiently alkaline to allow the formation of enediols which are the reactive species.

This results in many advantages, not the least of which is a restricted use of alkali.

The reason for this is that it is often necessary, at the end of the alkaline oxidative degradation reaction, to bring the pH of the reaction medium to about neutrality and even further to acidic pHs when it is desired to eliminate by distillation the formic acid inevitably produced. This therefore also results in an economy of acid and a reduced production of the by-products, namely the salts resulting from this neutralization or acidification.

This restricted use of alkali also has the effect, when the oxidative alkaline degradation reaction according to the invention is carried out on polymers, to treat this polymer skeleton carefully and to preserve the molecular weight of these polymers.

It results therefrom that the process of the invention makes it possible to obtain, as novel industrial products, polysaccharide acid derivatives, that is to say polymers composed of at least three carbohydrate units, containing less than 1% of residual reducing sugars and preferably less than 0.5% of residual reducing sugars, characterized in that their end carbohydrate is an aldonic acid containing one carbon atom less than the reducing carbohydrate from which it was derived.

The process of the invention may thus be carried out preferably with amounts of alkalis less than three mol of hydroxyl anions OH⁻ per mole of reducing sugar subjected to the oxidation. These amounts of alkali are preferably between 2.05 and 2.5 mol and preferentially between 2.2 and 2.4 mol.

Amounts above three mol of hydroxyl anions OH– per mole of reducing sugar used appear to be of no value since they are uneconomical and since they even prove to be harmful, in particular in the case of an oxidative degradation carried out on polysaccharides. The reason for this is that, in this case, attack of the polymer skeleton of the polysaccharides and a lowering of their molecular weight are observed.

Amounts lower than two mol of hydroxyl anions OH⁻ per mole of reducing sugar used no longer make it possible to obtain a complete alkaline oxidative degradation and their use results in a reaction which, although selective, is incomplete and is reflected by the persistence of residual reducing sugars at the end of the reaction.

However, when this presence of residual reducing sugars is not a handicap in the case of certain products obtained by the process of the invention, it may be envisaged to use amounts of alkali less than two mol of hydroxyl anions OH⁻ per mole of reducing sugar used. This may be the case in particular when it is envisaged to purify the aldonate obtained, for example by crystallization.

The temperature at which the process of the invention is carried out is generally between 10° and 80° C. It is preferred to work between 20° and 70° C. and even more preferably between 25° and 60° C.

It should be noted as a general rule that the lowest temperatures allow the best selectivities to be obtained, but this occurs to the detriment of the rate of reaction. Conversely, higher temperatures allow the reaction times to be shortened and may be used insofar as a slight degradation of a polymer or the production of a few percent of carbonic acid, oxalic acid, glyceric acid, glycolic acid, lactic acid, erythronic acid, metasaccharinic acid, dihydroxybutyric acid, etc. are not harmful to the product obtained or to the use intended to make of it.

However, a preferred use of this process, which makes it possible to combine both the specificity of the reaction and the rapid removal of all the reducing sugars, consists in starting the alkaline degradation reaction at about 40° C. and in increasing this temperature gradually or by stages up to 60° C. progressively as these reducing sugars are removed as a result of their oxidation into aldonic acid of immediately lower order. In general, it is preferred to allow the reaction to continue until a reducing sugar content, measured by the Bertrand method, of less than 1%, preferably of less than 0.5% and even more preferably of 10 less than 0.3%, is obtained, this content being expressed as a weight percentage of glucose equivalent on the sugar solids introduced into the reactor.

The solids concentration at which it is convenient to carry out the process according to the invention is not critical and should above all be guided by economic principles. Concentrations below 50 g of solids per liter of reaction medium are generally not advantageous since, in this case, they call upon the use of too large a reactor volume. Similarly, concentrations above 600 g/l may generally not be envisaged since, in this case, they require an aeration power and a stirring power which are such that the mechanical stresses they impose cannot find an inexpensive solution.

Here also, a practical implementation of the process of the invention consists in starting this oxidative degradation in the presence of small amounts of reducing sugars and then in introducing these into the reactor continuously or portionwise, in the form of powder or concentrated syrups, progressively as they disappear and are converted into aldonic acid of immediately lower order.

The reactors which enable the process of the invention to be carried out are reactors which allow efficient heat and mass transfers and may be those which are used for the aerobic microbiological conversion of various liquid substrates either into biomass or into organic amino or non-amino acids, or into enzymes or into antibiotics.

Since the essence of the invention lies in the fact that the air is stir-beaten and introduced into the reaction medium under stirring and aeration conditions such that this reaction medium has a pink color for as long as possible, these conditions should be permanently adapted to the reaction progress.

At constant temperature, since the oxidation is faster at the start of the reaction than at the end of the reaction, the oxidation reaction should be started by stirring and/or aerating the reaction medium vigorously. Next, as this reaction proceeds, care will be taken to maintain this pink color by decreasing the aeration or the stirring while being careful, however, to ensure that the reaction medium never becomes red.

For constant stirring and/or aeration, care may be taken to maintain this pink color by varying the temperature of the reaction medium. An increase in temperature has the effect of increasing the rate of oxidation and of decreasing the oxygen solubility. When the reaction medium tends to become colorless, the pink color may readily be re-established by increasing this temperature. Conversely, when the reaction medium becomes too red, this temperature will be lowered.

In order to carry out the process of the invention, it is preferred to use an amount of SAM generally representing from 0.1 g to 5 g per mole of reducing sugar used and expressed in the form of glucose equivalent. Preferably, this amount of SAM is between 1 g and 4 g per mole of reducing sugar and, even more preferably, between 2 g and 3 g per mole of reducing sugar.

The amount of hydrogen peroxide is used simultaneously with the SAM and in substantially equimolar amount. Thus, generally from 0.03 ml to 1.6 ml, preferably from 0.3 ml to 1.2 ml and even more preferably from 0.5 ml to 1 ml of 110-volumes hydrogen peroxide will be used per kg of substrate to be oxidized.

Since the SAM and the hydrogen peroxide have a catalytic role, their concentrations in the reaction medium may also be varied in order to adapt the oxidation rates to the mechanical performance of the reactors used. For example, if a reactor which is only of low installed aeration and stirring power is used, it will be advantageous to use only the weakest possible doses of the catalyst pair.

A preferred way of carrying out the alkaline oxidative degradation of the reducing sugars according to the process of the invention consists in introducing these sugars gradually into the reaction medium.

Thus, with constant stirring, aeration and temperature, it is possible to maintain the pink color of the SAM by adjusting the introduction flow rate of the reducing sugar into the alkali solution. Too high an introduction flow rate will make the SAM turn dark red whereas too low a flow rate will make the medium colorless.

The Applicant Company has observed that the best embodiment of the process of the invention consists an firstly introducing into the reactor, in the form of an aqueous solution, a part, generally less than 25%, preferably less than 15% and even more preferably less than 10%, of the reducing sugar or of the polymer which it is envisaged to oxidize, and then in aerating under aeration and stirring conditions which are determined experimentally this dilute solution of sugar or of polymer. It is convenient to exploit this period of saturation of the medium with dissolved oxygen in order to bring this "stock solution" to the correct temperature. After this period, which generally does not exceed half an hour, it is preferred to add in a single portion the dose of alkali required for the oxidative degradation reaction of the reducing sugar or of the polymer which it is envisaged to use, by calculating this dose such that it corresponds to about 2.3 mol of hydroxyl anions OH⁻ per mole of reducing sugar. This alkali is calculated in slight excess so as to conserve to the end of the reaction an alkalinity reserve which is sufficient to allow the formation of enediols, which are intermediates in this oxidation reaction. This alkali may also be added continuously or portionwise during the reaction, but the usefulness of this cannot clearly be seen, especially in the case of the oxidation of non-polymer materials.

Preferably, the SAM is introduced into the reactor at the same time as the alkali and the hydrogen peroxide. It is preferred to introduce this SAM directly into the reactor in powder form.

The reaction medium then immediately turns a deep red color which disappears after a few tens of seconds to become pink again.

At this point, continuous or portionwise introduction of the remaining reducing sugars is then begun, it being possible for this remainder to represent at least 75%, preferably at least 85% and even more preferably at least 90%, of the reducing sugar or of the polymer which it is envisaged to oxidize. The flow rate at which these remaining reducing sugars, which may either be in concentrated solution form or in powder form, is added is adjusted in order to be adapted to the stirring and aeration performance of the reactor and is generally such that the substrate to be oxidized is totally introduced in 1 to 10 hours, preferably in 2 to 8 hours and even more preferably in 3 to 6 hours.

When all of the substrate to be oxidized has been introduced into the reactor and when the reaction has reached a sufficient degree of progress such that at least 90% of the reducing sugars introduced have been converted into aldonic acid of immediately lower order, the temperature of the reaction medium may be increased gradually in order to complete this reaction as quickly as possible, while at the same time taking care to maintain this pink color of the reaction medium. The reaction is stopped when the content of reducing sugars has fallen below a sufficiently low value, less than 1% of glucose equivalent in most cases.

Depending on its destinations or its uses, the crude reaction medium thus obtained may undergo various types of processing or purification.

In an essentially general manner, the SAM should be removed. This may be carried out extremely simply by adsorption of this catalyst onto vegetable or animal charcoal. The best way of proceeding consists in percolating the reaction medium through columns of granular charcoal after the pH of this reaction medium has been brought to a value preferably below 7.0.

If the formic acid proves to be a nuisance in the products obtained by the process of the invention, it is convenient to remove it by distilling the reaction medium after it has been acidified with a strong acid and opt onally crystallized and the salt formed by this strong acid and the alkali used during the oxidation reaction have been removed.

However, such a purification is not necessary when it is desired to use the aldonates or the aldonate polymers obtained by the process of the invention in applications such as detergency or fluidity modifiers or setting-time modifiers for concretes, mortars and cements.

This purification, which consists especially in removing the formic acid, may be necessary insofar as it is envisaged to hydrogenate the aldonic acids obtained in order to obtain the corresponding polyols. This may be the case, for example, of xylitol, which may be obtained by hydrogenation of xylonic acid lactone, it being possible for this acid to be produced under economic and purity conditions that are unequalled by the process of the invention by oxidizing L-sorbose.

The aim of the examples which follow is to illustrate and to afford a better understanding of the invention. They should not be considered as limiting, in particular as regards the conditions cf aeration or of stirring of the reactors which allow the process of the invention to be carried out.

In particular, the geometry and size of the reactors used have a great influence on the invariable similarities consisting, in particular, of the Reynolds number, and thus on the capacities of the apparatus to transfer the oxygen required for the process of the invention into the liquid medium.

EXAMPLE 1

Oxidation of a monomer: glucose.

7 liters of water and 338.60 grams of dextrose monohydrate (i.e. 1.71 mol of glucose) are introduced into a Biolafitte glass fermenter tank with a working capacity of 15 liters. This solution is aerated with a flow rate at air corresponding to 20 liters per minute and with stirring at 650 revolutions/minute while maintaining its temperature at 40° C.

A glucose solution containing 50% solids, prepared using 1443.40 grams of dextrose monohydrate and 1181 grams of water, thus containing 7.29 mol of glucose, and a concentrated 50% sodium hydroxide solution made from 840 g of dry sodium hydroxide and 840 g of water, i.e. 21 mol of sodium hydroxide, are prepared at the time of use. 24 g of sodium anthraquinone 2-sulfonate are weighed out and 7.56 cm$^3$ of 110-volumes hydrogen peroxide (30% concentration) are prepared.

At time t=0, corresponding to about 30 minutes of aeration of the glucose solution contained in the fermenter, the concentrated sodium hydroxide solution, the anthraquinone and the hydrogen peroxide are simultaneously added to the fermenter.

The reaction medium then immediately turns a dark red color characteristic of the reduced form of SAM : SAM (OH)_. This color disappears almost immediately on bringing the stirring to a speed of 800 revolutions per minute and the reaction medium becomes colorless, characterizing the oxidized form of SAM:SAMO A pink color of the medium is immediately reestablished by lowering the stirring speed to 415 revolutions per minute, and the concentrated 50% glucose solution is then introduced continuously into the reactor.

Care is taken from that point to the end of the reaction to ensure that the reaction medium permanently has a pink color by permanently adjusting the stirring speed to a suitable value.

When the reducing sugar content of the reaction medium has fallen to a value close to 10 g/liter, which occurs after 180 minutes, the temperature is gradually increased to 60° C.

For greater convenience, the values of the temperatures and of the stirring speeds used in carrying out this example are given in the table below, as a function of time. The approximate flow rate of introduction of the concentrated glucose solution into the fermenter is also indicated in this table:

TABLE 1

| Time in minutes | temperature °C. | stirring (revolutions/min) | flow rate of the glucose solution ml/min |
|---|---|---|---|
| 0 | 38.7 | 415 | 10.1 |
| 5 | 38.7 | 415 | 10.1 |
| 14 | 39.1 | 420 | 10.1 |
| 20 | 39.7 | 430 | 10.1 |
| 30 | 40 | 445 | 10.1 |
| 40 | 40 | 465 | 10.1 |
| 41 | 40 |  | 13.3 |
| 45 | 40 | 475 | 13.3 |
| 70 | 40 | 475 | 13.3 |
| 74 | 40 | 500 | 13.3 |
| 79 | 40 | 520 | 13.3 |
| 170 | 40 | 590 | end of the addition |
| 180 | 45 | 725 |  |
| 188 | 45 | 775 |  |
|  | 50 | 890 |  |
|  | 50 | 855 |  |
|  | 50 | 835 |  |
| 212 | 50 | 800 |  |
| 216 | 50 | 765 |  |
| 219 | 50 | 735 |  |
| 220 | 50 | 695 |  |
| 225 | 50 | 630 |  |
| 229 | 50 | 595 |  |
| 234 | 50 | 550 |  |
| 250 | 50 | 445 |  |
| 255 | 50 | 430 |  |
| 257 | 50 | 405 |  |

TABLE 1-continued

| Time in minutes | temperature °C. | stirring (revolutions/min) | flow rate of the glucose solution ml/min |
|---|---|---|---|
| 265 | 50 | 380 |  |
| 280 | 50 | 335 |  |
| 290 |  | 300 |  |
| 310 | 55 | 500 |  |
| 312 | 60 | 350 |  |
| 320 | 60 | 250 |  |
| 355 | 60 | 220 |  |

In this example, in which the alkali/sugar ratio was set at 21/9 mol, i.e. 2.33 mol of hydroxyl anions per mole of reducing sugar used, and in which the sugar used at the start of the reaction represented 19% of the total amount subjected to oxidation, the glucose was oxidized to arabinonic acid in a molar yield of 84.7%.

Only 2% of the molar yield of agLyceric acid and 6.4% of the molar yield of glycolic acid were obtained.

As a comparative example, it will be noted that Vuorinen et al. (Starke, 43 No. 5, pp. :94–198), in carrying out the oxidation of glucose without methanol, had to use a pressure of pure oxygen of 26 bar in order to obtain an arabinonic acid yield of 78% only with 3.5% and 6.5% impurities consisting of glyceric acid and glycolic acid respectively.

In the present example, at time t =280 min, the reducing sugar concentration of the reaction medium was 3.4 g/l; it was only 0.5 g/l at time t =355 min when the reaction was stopped, which represents about 2.2% and 0.32% of residual reducing sugars respectively relative to the glucose used, given that the total reaction volume at the end of the oxidation was 10.5 liters.

At the end of the reaction, this reaction medium was neutralized using 40 ml of concentrated sulfuric acid in order to achieve a pH of 5.80. The solution obtained then turns green.

The medium thus neutralized is then percolated through a granular charcoal column which makes it entirely colorless and removes the SAM therefrom.

Simple concentration to a solids content of greater than 30% allows the sodium arabinonate to be crystallized.

Complete dehydration of this reaction medium thus purified makes it possible to obtain a powder therefrom which can be used as a "co-builder" in washing formulations. Its very low residual reducing sugar content does not result in any coloration of the formulae over time.

EXAMPLE 2

Oxidation of a polymer: glucose syrup.

9.190 liters of water and 481 g of an aqueous solution of a 37 DE glucose syrup consisting of 1532.6 g of this glucose syrup with a solids content of 78.5% and 873.7 g of water are introduced into the same equipment as that described in Example 1. This solution is aerated for 30 minutes with a flow rate of air fixed at 20 1/min and with stirring of 650 revolutions/minute while maintaining its temperature at 40° C.

A solution of 50% sodium hydroxide made from 217.6 g of sodium hydroxide and the same amount of water is prepared at the time of use.

At time t=0 corresponding to 30 minutes of aeration of the glucose syrup solution, the sodium hydroxide solution, 6.6 g of SAM and 2.2 cm³ of 110-volumes hydrogen peroxide solution are introduced simultaneously into the fermenter.

The reaction medium then immediately turns blood-red for a few seconds and then decolorizes.

The stirring is then lowered to a speed of 400 revolutions/minute in order to give the reaction medium a pink color.

After 10 minutes of reaction, the remaining glucose solution is added at a flow rate such that this addition takes place in 3 hours.

Throughout the reaction, the stirring speed is adjusted permanently in order to maintain a pink color in the medium.

After 3 hours and 20 minutes of reaction, the temperature of the reaction medium is increased to 50° C. and, after five hours of reaction, it is increased to 60° C. Lastly, the reaction is stopped after 6 hours 40 minutes. The reducing sugars content of the reaction medium has then fallen to 0.36 g/100 g of glucose syrup solids.

In this example, in which the alkali/reducing sugar molar ratio was set at 2.2, it was possible to oxidize all of the glucose syrup into arabinonate and dextrin-arabinonate while retaining the degree of polymerization of the glucose syrup subjected to oxidation, that is to say without any detectable hydrolysis of the oside linkages appearing. This novel product is obtained in an entirely reproducible manner and does not become colored, even when placed in strongly alkaline medium.

EXAMPLE 3

Oxidation of a ketose: sorbose.

L-sorbose is oxidized by introducing 7470 g of water, which were aerated for 30 minutes at 25° C., into the reactor used in the above examples.

768 g of an aqueous 50% sodium hydroxide solution (9.6 mol), 4 cm³ of 110-volumes hydrogen peroxide and 12 g of SAM were then added thereto. 1440 g of a 50% sorbose solution (4 mol) were lastly added to the contents of this reactor. The sodium hydroxide/sugar molar ratio was thus 2.4. This sorbose solution was added at a flow rate of 6 g/min. All of the sugar was thus introduced in 4 hours, at the end of which the temperature was increased to 50° C. The reaction was stopped after 8 hours. Throughout this time, the reactor was aerated with a flow rate of air of 20 liters/min and the stirring was adjusted to between 800 and 190 revolutions/minute so as always to maintain a pink color in the medium.

At the end of the reaction, a residual reducing sugar content of 0.17% was obtained and a yield of sodium xylonate of 75 mol% was observed.

EXAMPLE 4

Oxidation of a modified starch hydrolysate: carboxymethyl starch.

A carboxymethyl wheat starch with a degree of substitution of 0.22 was hydrolyzed enzymatically using 1% Termamyl 120 LS alpha-amylase marketed by the company Novo, until a dextrose equivalent of 25.6 is obtained.

After filtration and decolorization of this syrup according to standard processes, it was oxidized in the same equipment as that described in Example 1.

After aerating and bringing 5124 g of water to 40° C. in the reactor, 768 g of aqueous 50% sodium hydroxide solution (9.6 mol) and 12 g of SAM and 4 cm³ of 110-volumes hydrogen peroxide were added thereto. 4320 cm³ of an aqueous solution containing 50% carboxymethylstarch hydrolysate containing 2808 g dry of this 25.6 DE product (i.e. 4 mol of reducing sugars expressed as glucose), were then introduced at a flow rate of 13.7 ml/min.

Throughout the reaction, which lasted ten hours, care was taken to maintain the color of the medium.

At the end of the reaction, a residual reducing sugar content of 0.1% and no change in the average degree of polymerization of the starch hydrolysate were observed.

After rectification of the pH to 6.0 and then purification on a column of granular charcoal in order to remove the SAM and, lastly, spraying of the product, this product was used as a replacement for polyacrylates in a washing formula by replacing 1 part of polyacrylates with 2 parts of the novel carboxymethylstarch hydrolysate oxidized according to the invention.

Not only do the powders obtained not become colored on storage, but they also exhibit very advantageous washing qualities since, after 25 consecutive washes of samples of cotton and cotton/polyester fabric were carried out, the whiteness indices obtained proved to be higher than the polyacrylate control.

In addition, the degree of organic encrustation of the fabrics turns out to be significantly lower.

We claim:

1. A process for the alkaline oxidative degradation of an ose, a ulose, their polymers or their mixtures, in aqueous solution in the presence of a redox pair consisting essentially of a mixture of 2-anthraquinone monosulfonic acid and hydrogen peroxide, wherein oxidizing gas is air and said air is stir-beaten and introduced into the reaction medium under stirring conditions and at a flow rate such that the oxygen saturation of the reaction medium leads to the production of a pink color in this reaction medium.

2. The process according to claim 1, wherein said process is carried out with amounts of alkali of less than three moles of hydroxyl anions per mole of reducing sugar used.

3. The process according to claim 2, wherein the amounts of alkali are between 2.05 and 2.5 mole of alkali per mole of reducing sugar used.

4. The process according to claim 3, wherein the amounts of alkali are between 2.2 and 2.4 mole of alkali per mole of reducing sugar used.

5. The process according to claim 1, wherein said process is carried out at a temperature of between 10° and 80° C.

6. The process according to claim 5, wherein said process is carried out at a temperature of between 20° and 70° C.

7. The process according to claim 6, wherein said process is carried out at a temperature of between 25° and 60° C.

8. The process according to claim 1, wherein the alkaline oxidative degradation is initiated in the presence of small amounts of reducing sugars and is then continued by introducing these into the reactor continuously or portionwise, in the form of powder or concentrated syrups, progressively as they are removed and are converted into aldonic acid of immediately lower order.

9. The process according to claim 1, wherein 2-anthraquinone monosulfonic acid is used at a concentration representing 0.1 g to 5 g per mole of reducing sugar used and expressed in the form of glucose equivalent.

10. The process according to claim 9, wherein 2-anthraquinone monosulfonic acid is used at a concentration representing 1 g to 4 g per mole of reducing sugar expressed in the form of glucose equivalent.

11. The process according to claim 10, wherein 2-anthraquinone monosulfonic acid is used at a concentration representing 2 g to 3 g per mole of reducing sugar expressed in the form of glucose equivalent.

12. The process according to claim 1, wherein the hydrogen peroxide solution is used simultaneously with the 2-anthraquinone monosulfonic acid and in substantially equimolar amounts.

* * * * *